United States Patent [19]
Merkle et al.

[11] Patent Number: 5,527,536
[45] Date of Patent: Jun. 18, 1996

[54] ACTIVE INGREDIENT PATCH FOR LOW-MELTING AND/OR VOLATILE ACTIVE INGREDIENTS

[75] Inventors: Hans P. Merkle, Zurich, Switzerland; Klaus Nagels, Bonn, Germany; Dietrich Schacht, Cologne, Germany; Hans-Michael Wolff, Monheim, Germany

[73] Assignee: Schwarz Pharma AG, Monheim, Germany

[21] Appl. No.: 367,262

[22] PCT Filed: Jul. 17, 1993

[86] PCT No.: PCT/DE93/00638

§ 371 Date: Feb. 27, 1995

§ 102(e) Date: Feb. 27, 1995

[87] PCT Pub. No.: WO94/02123

PCT Pub. Date: Feb. 3, 1994

[30] Foreign Application Priority Data

Jul. 23, 1992 [DE] Germany ............ 42 24 325.4

[51] Int. Cl.6 .................................................. A61F 13/00
[52] U.S. Cl. ........................................... 424/448; 424/449
[58] Field of Search ................................ 424/448, 449

[56] References Cited

U.S. PATENT DOCUMENTS

| | | | |
|---|---|---|---|
| 4,485,077 | 11/1984 | Martinez | 423/320 |
| 4,668,232 | 5/1987 | Cordes | 604/897 |
| 4,668,332 | 5/1987 | Ohnuki et al. | 156/360 |
| 5,032,403 | 7/1991 | Sinnreich | 424/448 |
| 5,126,144 | 6/1992 | Jaeger | 424/448 |
| 5,354,597 | 10/1994 | Capik | 428/152 |

FOREIGN PATENT DOCUMENTS

| | | | |
|---|---|---|---|
| 0186071 | 7/1986 | European Pat. Off. | A61F 13/02 |
| 0186019 | 7/1986 | European Pat. Off. | A61L 15/06 |
| 0249979 | 12/1987 | European Pat. Off. | A61L 15/06 |
| 0305757 | 3/1989 | European Pat. Off. | A61L 15/03 |
| 0439180 | 7/1991 | European Pat. Off. | A61L 15/16 |
| 0144486 | 11/1991 | European Pat. Off. | A61F 13/00 |
| 0521761 | 1/1993 | European Pat. Off. | A61L 15/30 |
| 3743947 | 3/1989 | Germany | A61K 15/44 |
| 63-203616 | 8/1988 | Japan | A61K 31/415 |

*Primary Examiner*—D. Gabrielle Phelan
*Attorney, Agent, or Firm*—Marshall, O'Toole, Gerstein, Murray & Borun

[57] ABSTRACT

The invention concerns a patch for the controlled release of readily available volatile active substances to the skin, the patch comprising a back layer and, bonded to it, a water-insoluble adhesive film consisting of a pressure-sensitive fusion adhesive, plus a detachable film covering the adhesive film. The patch is characterized in that the pressure-sensitive fusion adhesive contains a triple-block copolymer of polystyrene block copoly(ethylene/butylene) block polystyrene (SEBS) at a concentration of 10 to 80% by wt., and an active substance which, at the temperature at which the adhesive bonds, is a readily volatile liquid, and which is present at a concentration of 2.5 to 25% by wt.

16 Claims, No Drawings

ACTIVE INGREDIENT PATCH FOR LOW-MELTING AND/OR VOLATILE ACTIVE INGREDIENTS

This application is a 371 of PCT/DE93/00638, filed Jul. 17, 1993.

DESCRIPTION

The present invention is concerned with an active ingredient patch for controlled topical or transdermal release of volatile active ingredients, consisting of a backing layer or carrier layer and a reservoir layer bonded to it, which consists of an SEBS three-block copolymer which serves at the same time as adhesive layer and control layer for the release of the active ingredient, and method for the production of this active ingredient patch from the melt. The skin patch is covered with a protective film, which is removed by peeling it off from the reservoir layer before the use of the patch, that is, before application of the patch on the skin.

Active ingredient patches, which permit controlled release of the active ingredient(s) into the skin are already known from the literature. Embodiments of such patches, in which the active ingredient is dissolved or dispersed homogeneously in a thin contact (pressure-sensitive) adhesive layer and is liberated from it in a diffusion-controlled manner, are transdermal or topical systems of simple design, suitable in principle for mass production.

However, in practice, the development and/or production of such active ingredient patch always has disadvantages, of which are described below, and as a result, it is correspondingly expensive:

The adhesive properties of the reservoir layer cannot be adjusted optimally at high active ingredient contents, so that the patch must have an additional adhesive layer in order to achieve good adhesion on the skin surface during use and to permit complete painless removal of the patch from the skin after use.

The reservoir must have a multilayer structure in order to be able to incorporate sufficient amounts of active ingredient into the patch and/or additional depots are to be provided which are separated spatially and functionally from the adhesive layer.

An additional control layer is necessary in order to ensure controlled, continuous liberation of the active ingredient over long application time periods and/or at least to limit skin irritation and/or systemic side effects at a given active ingredient release rate per unit time.

The contact adhesive reservoir layer is prepared from solution, so that there is the problem of elimination of solvent residues and the related evaporation of volatile active ingredients. The use of solvents in the production of active-ingredient-containing contact adhesive layers is disadvantageous for several reasons. The preparation of the solution requires at least one technologically expensive process step. For medical purposes, highly pure and thus expensive solvents must be used for the dissolution of the adhesive or of its starting materials, in order to ensure the corresponding absence of residues in the adhesive reservoir. Another problem is to achieve absence of solvent in the patch itself. Therefore, technically expensive drying sections and aspiration installations are necessary. In addition, recovery and separation of the solvent must be ensured technologically in order to avoid environmental pollution; moreover, the combustibility of solvents represents an additional risk. Furthermore, most organic solvents are damaging to the human organism, so that expensive protective measures must be provided for the personnel involved in manufacture.

Skin patches, among others, for transdermal application of bupranolol, are known from EP 0144486; here, the active ingredient is contained in a reservoir with multistep structure, whereby a multistep active ingredient concentration gradient from the outer reservoir layer that faces the carrier film to the skin is provided as control element for the release of the active ingredient.

U.S. Pat. No. 4,668,232 also describes, among others, an active ingredient patch with β-blockers in which an adhesive reservoir containing bupranolol or propranolol is built up in two partial steps; in this case, water-swellable polymers are added to the reservoir to improve and control its active ingredient release properties.

Transdermal release systems with the β-blocker timolol are known from EP 0186071, which, for reasons of local tolerance, limit the liberation of active ingredient from the reservoir to a maximum of 20 µg/cm$^2$/h with the aid of discrete control layers.

The disadvantages related to the use of solvents in the development and production of active ingredient patches are to be avoided by the production of self-adhesive active ingredient reservoirs from the melt. Thus, for example, indomethacin-containing contact hot-melt adhesives are known from US 4,485,077 and JP 63203616 describes contact hot-melt adhesives for patches and similar structures, especially for etofenamate. According to DE-P 37 43 947, the two proposed forms of application for contact hot-melt adhesives are suitable for high processing temperatures, but not for low-melting and/or volatile active ingredients, such as, for example, the sensitive nicotine, which has a low boiling point and high evaporation rate. DE-P 37 43 947 describes correspondingly a method in which the nicotine reservoir is produced using a contact hot-melt adhesive with a processing temperature of 40°–80° C. Various nicotine patches have been described with and without nicotine depots, which are spatially and functionally separated from the adhesive layer. The above application does not give examples from which the loading of contact hot-melt adhesives with active ingredient could be deduced in single-layer systems, nor are there data on the loading capacity of such adhesive formulations. Rather, it is described that the devices named there also have one or several nicotine depots in which nicotine is present at concentrations which are higher than that of the nicotine-containing contact hot-melt adhesive layer, as a result of which higher doses of nicotine can be incorporated and thus the device can be used for a longer period of time before it has to be replaced. The incorporation of an additional depot in a patch requires additional technological expenditure and consequently development and production become more expensive.

EP 0 521 761 discloses a special dressing that promotes wound healing, consisting of a synthetic polymer matrix, which is formed from a mixture of block copolymers of the S-EB-S type, with plasticizer.

The inventive idea here is to provide such a matrix wound dressing which protects the wound against the outside environment and retains wound exudations, but is able to provide a moist medium. The reason is that this is advantageous for growth and cell multiplication, without sticking to the wound, so that damage of the skin trauma is avoided when the dressing is removed, while, at the same time, formation of the covering tissue is promoted under good conditions.

Although, here, block copolymers of the S-EB-S type are mentioned, they are always named in a mixture with plasticizer and these are used exclusively as adhesive material.

Finally, it should be indicated that the claimed composition could contain pharmaceutically active ingredients in therapeutically active amounts. However, loading of the adhesive with active ingredients, data as to which active ingredients or active ingredient groups can be used, or data regarding the loading capacity of such adhesive formulations are lacking.

EP 0 356 382 describes a multilayer patch, the reservoir layer of which, that is able to release the active ingredient, is formed from a mixture of styrene/mixed block copolymers with alkane or alkadiene homopolymers. Additionally, this reservoir layer must contain at least one agent that promotes the permeability of skin to active ingredients. Optionally, other control means, for example, a membrane, must be present.

For the reasons given above, such a patch structure is not only difficult to produce industrially, but is undesirable because of the skin penetration promoters that are necessarily contained in it.

European Offenlegungsschrift EP 0 249 979 discloses a hot-melt adhesive of the type A-B-A (three-block copolymer) or A-B-A-B-A-B (multiblock copolymer), which is suitable for use in absorption devices that are to be secured on tissues. For example, sanitary napkins or diapers are named as such means. For these applications, a number of additives are necessarily added to the block copolymers mentioned above.

The indication that these types of adhesives could contain pharmaceutically active ingredients cannot be deduced from this document. Mention of the fact that these types of adhesives could serve as adhesive and control layer for pharmaceutically active ingredients is lacking.

EP 0 186 019 describes an active-ingredient-containing patch system which contains water-swellable polymers that are not soluble in the adhesive film. The addition of these special swellable polymers provides reproducible release of the active ingredient, controlled over the entire application time period, in a high, therapeutically appropriate amount of active ingredient.

Sometimes the use of a three-block polystyrene poly(ethylene butylene) polystyrene copolymer of the SEBS type is described. However, this polymer is used exclusively in organic solvents as a necessary admixture to water-swellable polymers. According to the teaching of this document, it is only the combination consisting of this adhesive composition, the swellable polymer and organic solvent that is able to provide an active ingredient patch that ensures reproducible release of the active ingredient, controlled as much as possible over the entire application time period, at a high total amount of active ingredient.

Indication that the adhesive of the SEBS type could be used along for the production of therapeutically applicable active ingredient patches, without the addition of other substances that would control the loading with active ingredient and the amount of active ingredient released from the patch, cannot be deduced from this document.

Finally, EP 0 439 180 describes a transdermal therapeutic system with the active ingredient tulobuterol. In this document, styrene-1,3-diene-styrene block copolymers are used as polymer component. It can be deduced from the document that this polymer is suitable only for the galenic preparation form of a patch with the active ingredient tulobuterol, but not for the active ingredient salbutamol, which belongs to the same class of active ingredients, the β-sympathomimetics.

Furthermore, the block copolymer mentioned above is an elastomer, which contains chemically unsaturated groups as structural components and thus must be protected against oxidation and degradation due to shear stresses, even during processing. Added to this are protective measures in the finished patch as pharmaceutical during storage and limitations in the use of protective films. The patient demands transparent films that can be exposed to lights during application or to bath waters that contain sterilizing agents, for example, chlorine or ozone.

However, the document does not describe that copolymers of the SEBS type, which contain chemically saturated groups as structural components in the middle block, can be used generally in active ingredient patches, with the simultaneous function of adhesive and control layer for the release of active ingredients, while avoiding the above disadvantages, when they are used according to the invention, as described below.

Therefore the task of the present invention is to avoid the disadvantages of skin patches of this type for topical and/or transdermal application of low-melting and/or volatile active ingredients, especially of nicotine and of β-receptor blockers, such as bupranolol. It was found surprisingly that an active ingredient patch, without the addition of swellable polymers for controlled release of active ingredients into the skin, increases the loading capacity of the reservoir, without additional depots and control elements and/or control layers and no solvent, the patch consisting of a backing layer, of an adhesive film bonded to it consisting of a contact hot-melt adhesive, and of a layer that covers the adhesive film and can be removed again, while the adhesive layer contains a contact hot-melt adhesive, a three-block copolymer of polystyrene-block-copoly(ethylene-butylene)-block-polystyrene (SEBS) at a concentration of 10 to 80 weight %, preferably 20 to 40 weight %, and an active ingredient which is liquid at the processing temperature of the contact hot-melt adhesive, at a concentration of 2.5 to 25 weight %, also and contains optionally a tackifier. Preferably, the styrene content of the SEBS three-block copolymer is 10 to 50 weight % and especially preferably 10 to 30 weight %.

Furthermore, the adhesive film of the active ingredient patch according to the invention contains preferably between 20 and 90 weight %, especially preferably 40 to 70 weight % of a tackifier and optionally 0.1 to 1% anti-aging agent. Preferred tackifiers are aliphatic and/or aromatic hydrocarbon resins which are compatible with the end blocks and/or middle block of the SEBS polymer. Furthermore, preferably, hydroabietyl alcohol and/or its derivatives are used as tackifier.

Antioxidants, such as tocopherol, substituted phenols, hydroquinones, pyrocatechols and aromatic amines can be used as antiaging agents.

The active ingredient patch according to the invention can be produced by mixing the components of the contact hot-melt adhesive before the addition of the active ingredients while heating at 100° to 200° C., preferably 110° to 170° C., in an inert atmosphere, until a homogeneous melt is obtained and then dissolving the active ingredient in the melt of the contact adhesive under an inert gas at a processing temperature of 100° to 200° C., preferably 110° to 130° C. Preferably, the homogeneous, active-ingredient-containing contact hot-melt adhesive composition is applied onto the removable protective layer or onto an antiadhesive substrate by extrusion, casting, roll application, blade application, spraying or with a pressure process and covered with the backing layer. Another procedure consists in application of the homogeneous, active-ingredient-containing hot-melt adhesive composition onto the backing layer by extrusion, casting, roll application, blade application, spraying or by a pressure method and then covering it with the removable protective layer. Preferably, the individual patches are produced by cutting and/or format stamping.

Furthermore, it was found surprisingly that SEBS three-block copolymers with low-melting and/or volatile active ingredients, for example, nicotine or bupranolol, form reservoir layers which:

1. can be produced from the melt at processing temperatures above 100° C. without decomposition of the active ingredient and/or of the polymer, 2. can take up a large amount of active ingredient without the loss of their cohesiveness and adhesive strength, so that the incorporation of additional depot and/or active-ingredient-binding substances which are insoluble in the contact adhesive composition can be omitted, and 3. in which the release of the active ingredient can be adjusted to the required rate without additional control layers by adjusting the styrene content of the SEBS three-block copolymers and/or by the use of tackifiers, which are compatible with the end blocks and/or the middle block of the SEBS block copolymer.

Surprisingly, furthermore, when obtaining the SEBS-based active ingredient reservoir according to the invention from the melt, higher liberation rates from the patch are achieved than when the manufacturing process is from a solution, so that the amount of active ingredient in the reservoir can be reduced without lowering the release capacity of the patch in comparison to correspondingly structured and composed solvent-based systems. The technical expenditure and, consequently, the cost of the patch can be kept low by saving solvent, additional reservoir and control layers, as well as active ingredient. The invention is explained below with the aid of the following Examples:

EXAMPLES 1a to 1f

Production according to the hot-melt method

Kraton G 1657 (SEBS three-block copolymer), Regalrez 1094 (aliphatic hydrocarbon resin), Abitol (hydroabietyl alcohol) and Irganox 1010 (antioxidant) are melted under argon in a laboratory kneader at 110°–150° C. in the amounts given (see Table 1) and are mixed to obtain a homogeneous mixture (duration about 60 minutes). Then 23.9 g of bupranolol are dissolved in the clear melt under argon at 140° C. (duration about 20 minutes). The bupranolol-containing contact hot-melt adhesive composition is cast into a coolable mold coated with an antiadhesive layer to a film having a thickness of approximately 250 μm, cooled to 12°–14° C. within 5 minutes and covered with a 70 μm thick polyester film (backing layer). The open adhesive surface of the laminate thus obtained, consisting of adhesive film and backing layer, is then laminated to a 100 μm thick polyester film silicone-coated on both sides (=removable protective layer).

Then, individual patches with a surface area of 8 cm$^2$ are stamped out.

Comparison examples 1a' to 1f'

Preparation according to the solvent method

The components listed in Table 1, including bupranolol, are weighed into an iodine flask and dissolved in a mixture of 50 mL of petroleum benzine and 15 mL of toluene under shaking. The solvent-containing mass is coated onto a 100 μm thick polyester film with a doctor blade and dried for 3 days at 25° C. in a drying oven with air circulation, so that an adhesive film of approximately 174 g/m$^2$ results. The open adhesive surface of the laminate thus obtained, consisting of adhesive film and backing layer, is laminated to a 100 μm thick polyester removable film coated with silicone on both sides (removable protective layer).

Then individual patches with a surface area of 8 cm$^2$ are stamped.

TABLE 1

Composition of the hot-melt patch according to the invention and of the Comparison Examples

| Example (Comparison Example) | amounts in g · 10$^{-1}$ or in g for the Comparison Examples | | | | | |
|---|---|---|---|---|---|---|
| | Kraton GX # 1657 | Regalrez # 1094 | Abitol | Irganox # 1010 | bupranolol | total |
| 1a (1a') | 8.57 | 7.50 | 5.36 | 0.10 | 2.39 | 23.93 |
| 1b (1b') | 6.97 | 9.11 | 5.36 | 0.10 | 2.39 | 23.93 |
| 1c (1c') | 5.36 | 10.72 | 5.36 | 0.10 | 2.39 | 23.93 |
| 1d (1d') | 5.36 | 9.11 | 6.97 | 0.10 | 2.39 | 23.93 |
| 1e (1e') | 5.36 | 7.50 | 8.57 | 0.10 | 2.39 | 23.93 |
| 1f (1f') | 6.97 | 7.50 | 6.97 | 0.10 | 2.39 | 23.93 |

Release of active ingredient

Patch sections of 8 cm$^2$ in size are used for the measurement active ingredient release.

The test is carried out according to the Paddle-Over-Disk method according to USP XXII in 600 mL of phosphate buffer, pH 5.5, as release medium. Samples are taken every 15 minutes. The bupranolol content in the sample solution is determined by liquid chromatography.

The results of the release of active ingredient after 2, 4, 6, 8, 12 and 24 hours are summarized for Examples 1a to 1f in Table 2a, and for the corresponding Comparison Examples in Table 2b.

TABLE 2a

Release of active ingredient (hot-melt patch)

| Example | mean release in mg/8 cm² after | | | | | |
|---|---|---|---|---|---|---|
| | 2 h | 4 h | 6 h | 8 h | 12 h | 24 h |
| # 1a | 1.62 | 2.28 | 2.79 | 3.22 | 3.92 | 5.53 |
| # 1b | 1.20 | 1.67 | 2.02 | 2.31 | 2.80 | 3.91 |
| # 1c | 0.67 | 0.92 | 1.08 | 1.22 | 1.47 | 1.99 |
| # 1d | 0.87 | 1.18 | 1.41 | 1.60 | 1.92 | 2.65 |
| # 1e | 1.07 | 1.52 | 1.84 | 2.10 | 2.54 | 3.49 |
| # 1f | 1.29 | 1.79 | 2.18 | 2.50 | 3.02 | 4.17 |

TABLE 2b

Release of active ingredient (Comparison Examples)

| Comparison Example | mean release in mg/8 cm² after | | | | | |
|---|---|---|---|---|---|---|
| | 2 h | 4 h | 6 h | 8 h | 12 h | 24 h |
| # 1a' | 1.43 | 1.99 | 2.44 | 2.81 | 3.41 | 4.78 |
| # 1b' | 0.82 | 1.23 | 1.56 | 1.84 | 2.31 | 3.35 |
| # 1c' | 0.35 | 0.44 | 0.51 | 0.56 | 0.67 | 1.01 |
| # 1d' | 0.76 | 1.04 | 1.24 | 1.41 | 1.69 | 2.26 |
| # 1e' | 0.72 | 1.03 | 1.28 | 1.50 | 1.88 | 2.80 |
| # 1f' | 1.10 | 1.58 | 1.93 | 2.22 | 2.72 | 3.95 |

As shown by comparison of the measurement series in Table 2a and 2b, the release rates of the hot-melt patch are surprisingly above those of the solvent-based systems, sometimes clearly so, for the same composition and active ingredient concentration in the contact adhesive composition, at all measurement points, in spite of complete absence of solvent.

EXAMPLES 2a to 2f

Preparation according to the hot-melt method

Kraton G 1657 (SEBS three-block copolymer), Regalrez 1094 (aliphatic hydrocarbon resin), Kristalex F 85 (aromatic hydrocarbon resin), Abitol (tackifier) and Irganox 1010 (antioxidant) are melted under argon in a laboratory kneader at 110°–150° C. in the amounts given (see Table 3) and mixed until a homogeneous mixture is obtained (duration approximately 60 minutes). Bupranolol is dissolved in the given amount in the clear melt under argon at 140° C. (duration approximately 20 minutes). The bupranolol-containing contact hot-melt adhesive composition obtained in this way is cast into a heated, water-coolable mold with an antiadhesive coating to obtain an approximately 250 μm thick film, cooled to 12°–14° C. within 5 minutes and covered with a 70 μm thick polyester film (backing layer). The open adhesive surface of the laminate consisting of adhesive film and backing layer obtained in this way is laminated to a 100 μm thick polyester film silicone-coated on both sides (=removable protective layer).

Then individual patches with an area of 8 cm² are stamped out.

TABLE 3

Composition Example 2, end-block-resin-modified formulations (hot-melt patch)
Amounts given in g

| Example | Kraton GX # 1657 | Regalrez # 1094 | Kristalex # F85 | Abitol | Irganox # 1010 | bupranolol | total |
|---|---|---|---|---|---|---|---|
| 2a | 60.00 | 75.00 | 15.00 | 41.00 | 0.88 | 21.32 | 213.20 |
| 2b | 48.75 | 86.25 | 15.00 | 41.00 | 0.88 | 21.32 | 213.20 |
| 2c | 37.50 | 97.50 | 15.00 | 41.00 | 0.88 | 21.32 | 213.20 |
| 2d | 37.50 | 86.25 | 26.25 | 41.00 | 0.88 | 21.32 | 213.20 |
| 2e | 37.50 | 75.00 | 37.50 | 41.00 | 0.88 | 21.32 | 213.20 |
| 2f | 48.75 | 75.00 | 26.25 | 41.00 | 0.88 | 21.32 | 213.20 |

Release of active ingredient

Patch sections of 8 cm² in size are used for the measurement of the active ingredient release. The test is carried out according to the Paddle-Over-Disk method as described for Example 1. The results of the liberation of active ingredient after 2, 4, 6, 8, 12 and 24 hours are summarized for Examples 2a to 2f in Table 4.

TABLE 4

Active ingredient release, Example 2, end-block-resin-modified formulations (hot-melt patch) mg/8 cm²

| Example | 2 h | 4 h | 6 h | 8 h | 12 h | 24 h |
|---|---|---|---|---|---|---|
| # 2a | 1.06 | 1.47 | 1.79 | 2.06 | 2.51 | 3.55 |
| # 2b | 0.74 | 1.04 | 1.26 | 1.45 | 1.77 | 2.46 |
| # 2c | 0.44 | 0.61 | 0.74 | 0.84 | 1.01 | 1.37 |
| # 2d | 0.50 | 0.70 | 0.85 | 0.98 | 1.19 | 1.67 |
| # 2e | 0.60 | 0.84 | 1.02 | 1.18 | 1.43 | 2.01 |
| # 2f | 0.80 | 1.14 | 1.39 | 1.60 | 1.96 | 2.77 |

As the results shown in Table 4 indicate, the amount of active ingredient released can be retarded with the aid of aromatic hydrocarbon resins. The change of the amounts of SEBS polymer, and of aliphatic and aromatic hydrocarbon resins is possible in the art, so that the required release pattern can be achieved without having to incorporate additional control membranes.

At the same time, the required adjustments in the formulation can be made with regard to adhesive performance, permeability to water vapor and skin-compatible release behavior without having to change the amount of active ingredient contained.

EXAMPLES 3a to 3e and 4a to 4e

Preparation according to the hot-melt method

Kraton G 1657 (SEBS three-block copolymer) or Cariflex TR 1107 (SIS three-block copolymer), Regalrez 1094 (aliphatic hydrocarbon resin), Abitol (tackifier) and Irganox 1010 (antioxidant) are melted in a laboratory kneader at 110°–150° C. in the given amount (see Table 5) under argon and mixed until a homogeneous mixture is obtained (duration approximately 60 minutes). Then the adhesive composition is cast and cooled to 4° C.

A part of the produced adhesive composition is melted in the laboratory kneader at 110°–150° C. (duration approximately 10 minutes). The adhesive composition is diluted with Abitol, so that the quantitative composition shown in Table 6 is reached. Then the bupranolol amounts given in Tables 6 and 7 are added to the clear melts and dissolved under argon at 140° C. (duration approximately 20 minutes). The bupranolol-free or bupranolol-containing contact hot-melt adhesive composition thus obtained is cast into a heated, water-coolable mold with antiadhesive coating, to obtain an approximately 250 μm thick film, cooled to 12°–14° C. within 5 minutes and covered with a 70 μm thick polyester film (backing layer). The open adhesive surface of the laminate consisting of adhesive film and backing layer is then laminated to a 100 μm thick polyester film silicone-coated on both sides (removable covering layer).

Then individual patches with a surface area of 8 cm$^2$ are stamped.

TABLE 5

Composition Example 3, saturated middle block (hot-melt patch) Amounts given in g

| Example | Kraton GX #1657 | Cariflex TR #1107 | Regalrez #1094 | Abitol | Irganox #1010 | total |
|---|---|---|---|---|---|---|
| 3, a–e | 58.30 | | 79.58 | 61.20 | 0.92 | 200 |
| 4, a–e | | 58.30 | 79.58 | 61.20 | 0.92 | 200 |

TABLE 6

Composition Example 3, saturated middle block (hot-melt patch) Amounts given in g

| Example | Kraton GX #1657 | Regalrez #1094 | Abitol | Irganox #1010 | bupranolol | total |
|---|---|---|---|---|---|---|
| 3a | 29.17 | 39.83 | 30.54 | 0.46 | 0 | 100 |
| 3b | 28.42 | 38.80 | 29.83 | 0.45 | 2.50 | 100 |
| 3c | 27.69 | 37.80 | 29.07 | 0.44 | 5.00 | 100 |
| 3d | 26.23 | 35.81 | 27.54 | 0.41 | 10.00 | 100 |
| 3e | 23.32 | 31.81 | 24.48 | 0.36 | 20.00 | 100 |

TABLE 7

Composition Example 4, unsaturated middle block (hot-melt patch) Amounts given in g

| Example | Cariflex TR #1107 | Regalrez #1094 | Abitol | Irganox #1010 | bupranolol | total |
|---|---|---|---|---|---|---|
| 4a | 29.17 | 39.83 | 30.54 | 0.46 | 0 | 100 |
| 4b | 28.42 | 38.80 | 29.83 | 0.45 | 2.50 | 100 |
| 4c | 27.69 | 37.80 | 29.07 | 0.44 | 5.00 | 100 |
| 4d | 26.23 | 35.81 | 27.54 | 0.41 | 10.00 | 100 |
| 4e | 23.32 | 31.81 | 24.48 | 0.36 | 20.00 | 100 |

Dynamic-mechanical analysis

Characterization of the middle block temperature range

The active-ingredient-free or active-ingredient-containing adhesive compositions are characterized with the aid of dynamic-mechanical analysis. The amount of active ingredient contained was 2.5, 5, 10 and 20% bupranolol.

The determination of the dynamic-mechanical behavior in the temperature range of the middle block glass transition temperature was carried out with a Rheometrics RDS 7700 equipment. A PC was used for control equipment, which was operated with the software RHIOS 3.01. The operation was carried out in the parallel plate mode. The plate diameter was 8 mm. The frequency of the sinusoidal excitation was i Hz, that is, 6.28 rad/s. The temperature region measured was between −10° and 35° C.

The temperature was lowered in steps of 4° C. The initial temperature was 35° C. The temperature equalization time of the sample was 120 s. The tangent delta (damping), the maximum of tangent delta and the temperature of the maximum, the loss modulus and shear modulus were determined.

TABLE 8

Temperature at the maximum of tangent delta for the active-ingredient-free and active-ingredient-containing adhesive compositions of Examples 3 and 4

| Example | polymer | polystyrene (%) | bupranolol (%) | maximum tangent delta[a] (°C.) |
|---|---|---|---|---|
| 3a | Kraton | 14 | 0 | 7.8 |
| 3b | GX 1657 | | 2.5 | 8.2 |
| 3c | | | 5 | 7.3 |
| 3d | | | 10 | 7.6 |
| 3e | | | 20 | 7.5 |
| 4a | Cariflex | 15 | 0 | 7.4 |
| 4b | TR 1107 | | 2.5 | 8.0 |
| 4c | | | 5 | 7.3 |
| 4d | | | 10 | 7.0 |
| 4e | | | 20 | 5.1 |

[a]Measuring frequency 1 Hz.

The temperature at which the tangent delta reaches a maximum was determined for Cariflex TR 1107 and Kraton GX 1657. The results are presented in Table 8.

Characterization of the end block temperature range

The active-ingredient-free or active-ingredient-containing adhesive compositions were characterized with the aid of dynamic-mechanical analysis. The active ingredient content was 2.5, 5, 10 and 20% bupranolol. The determination of the dynamic-mechanical behavior in the temperature range of the use temperature (32° C.) and of the polystyrene glass transition was done with a Rheometrics RDS 7700. A PC was used as control equipment, which was operated with the software RHIOS 3.01. The operation was carried out in the parallel plate mode. The plate diameter was 25 mm. The frequency of the sinusoidal excitation was 1 Hz or 6.28 rad/s. The temperature range studied was between 25 and 130° C. The temperature was increased in steps of 6° C. The initial temperature was 25° C. The temperature equalization time of the sample was 90 s. The tangent delta (damping) of the loss modulus and shear modulus were determined.

TABLE 9

Temperature at which the shear modulus (G') falls below a value of 10,000 Pa. Measured values for Examples 3 and 4

| Example | polymer | polystyrene content, weight % | bupranolol, weight % | temperature (°C.) G' <10,000 Pa |
|---|---|---|---|---|
| 3a | Kraton | 14 | 0 | 82 |
| 3b | GX 1657 | | 2.5 | 77 |
| 3c | | | 5 | 74 |
| 3d | | | 10 | 71 |
| 3e | | | 20 | 62 |
| 4a | Cariflex | 15 | 0 | 63 |
| 4b | TR 15 1107 | | 2.5 | 62 |
| 4c | | | 5 | 58 |
| 4d | | | 10 | 56 |
| 4e | | | 20 | 32 |

Comparison of the measured values listed in Table 9 shows that the temperature at which the shear modulus drops below 10,000 Pa decreases to different degrees with increasing active ingredient content for comparable polystyrene contents. In the range of 10,000 Pa, the adhesive system goes into the molten state. The interval between the application temperature and the temperature of this transition gives an idea about the suitability of the adhesive composition as contact hot-melt adhesive. The value of the active-ingredient-free Cariflex TR 1107 lies in the range of Kraton GX 1657 containing 20 weight % of bupranolol.

While the temperature decrease for GX 1657 with saturated middle block is almost linear with increasing active ingredient content, in the case of TR 1107, when the bupranolol content goes above 10 weight %, surprisingly a large drop is observed. The temperature decrease is so large for the adhesive system based on TR 1107 containing 20 weight % bupranolol that the cohesiveness necessary for a contact adhesive system is no longer present in the range of application temperatures. Cohesiveness is lowered to the extent that the adhesive system separates from the carrier layer and leads to separation, and, on the other hand, when the adhesive system is separated from the skin, massive residues of adhesive composition remain on the skin.

TABLE 10

Shear modulus (G') of adhesive compositions based on GX 1657 at skin temperature (32° C.). The determination was carried out in the parallel plate mode. The plate diameter was 25 mm.

| Example | polymer | polystyrene (weight %) | bupranolol (weight %) | shear modulus at 32° C. (Pa) |
|---|---|---|---|---|
| 3a | Kraton | 14 | 0 | 1.14 E5 |
| 3b | GX 1657 | | 2.5 | 9.53 E4 |
| 3c | | | 5 | 1.02 E5 |
| 3d | | | 10 | 8.34 E4 |
| 3e | | | 20 | 5.32 E4 |
| 4a | Cariflex | 15 | 0 | 3.07 E4 |
| 4b | TR 1107 | | 2.5 | 3.08 E4 |
| 4c | | | 5 | 2.29 E4 |
| 4d | | | 10 | 2.46 E4 |
| 4e | | | 20 | 9.30 E3 |

Table 10 shows the results of the dynamic-mechanical characterization regarding the shear modulus at skin temperature (32° C.). Considering the literature (D. Satas (Ed.), Handbook of pressure-sensitive adhesive technology, Van Nostrand Reinhold, New York, p. 158 ff, 1989), good adhesive performance is expected when the shear modulus (G') lies between 50,000 and 200,000 Pa at the application temperature. Table 8 [Should be 10.–T] shows the results of the dynamic-mechanical characterization. While the measured values show that the formulation based on Kraton GX 1657 lies within these limits, the measured values for the formulation based on TR 1107 are clearly below the value of 50,000 Pa. At a degree of loading with 20% bupranolol, with Kraton GX 1657, according to the selected example of formulation, one can produce carrier systems which satisfy the requirements regarding the viscoelastic properties of an active ingredient patch. In the case of carrier systems based on Cariflex TR 1107, the viscoelastic properties are not in the required range at the application temperature for any of the listed examples of formulation, so that the requirements for a contact-adhesive reservoir are not satisfied.

EXAMPLES 5a, b and 6a, b

Preparation of the adhesive composition

Examples 5a, b

Kraton G 1657 (SEBS three-block copolymer) or Cariflex TR 1107 (SIS three-block copolymer), Regalfez 1094 (aliphatic hydrocarbon resin), Abitol (tackifier) are melted in a laboratory kneader at 160° C. in the given amounts (see Table 11) and the mixture is mixed until it becomes homogeneous (duration approximately 60 minutes). This process is carried out without entry of air, but a protective gas atmosphere is not used. Bupranolol is added to the clear melt. Then the mixture is mixed and/or kneaded further while air is entered over a large area. After 120, 180, 240, 300 and 360 minutes, samples of approximately 10 g are taken from the kneading trough to determine the molecular weight.

TABLE 11

Composition of Examples 5a and b Amounts given in g

| Example | Cariflex TR #1107 | Kraton GX #1657 | Regalrez #1094 | Abitol | bupranolol |
|---|---|---|---|---|---|
| 5a | 112.50 | | 75.00 | 50.00 | 12.50 |
| 5b | | 112.50 | 75.00 | 50.00 | 12.50 |

EXAMPLES 6a, b

Kraton G 1657 (SEBS three-block copolymer) or Cariflex TR 1107 (SIS three-block copolymer), Regalrez 1094 (aliphatic hydrocarbon resin), Abitol (tackifier) and Irganox 1010 (antioxidant) are melted in a laboratory kneader at 160° C. under argon in the given amount (see Table 12), and mixed until homogeneity is reached (duration approximately 60 minutes). Bupranolol is added to the clear melt. Then, the kneading is continued with the exclusion of air in an argon atmosphere. After 120, 180, 240, 300 and 360 minutes, samples of approximately 10 g are taken from the kneading trough. The molecular weight of the samples is determined with GPC.

TABLE 12

Composition Example 6a and b Amounts given in g

| Example | Cariflex TR #1107 | Kraton GX #1657 | Regalrez #1094 | Irganox #1010 | Abitol | bupranolol |
|---|---|---|---|---|---|---|
| 6a | 112.50 | | 75.00 | 1.25 | 50.00 | 12.50 |
| 6b | | 112.50 | 75.00 | 1.25 | 50.00 | 12.50 |

Molecular weight determination

The molecular weight determinations were carried out using gel permeation chromatography. The installation used consisted of a Lichrograph L-6000 HPLC pump (Merck, D Darmstadt), a column thermostat T-6300 (Merck), an ERC-7512 refractive index detector (Erma, J-Tokyo) and a D-2520 GPC integrator (Merck). A Polymer Laboratories (UK-Shropshire) PL-Gel 5 μ Mix Column was used.

The column was 300 mm long, the inside diameter was 7.5 mm; the particle size of the column filling was 5 μm. The calibration of the column was done with polystyrene, using a Polymer Laboratories Mole Standard: Polystyrene-medium Molecular Weight Calibration kit was used. Tetrahydrofuran served as solvent. The column temperature was 35° C., the pressure 25 bar; the flow rate of the solvent was adjusted to 1 mL/min.

The samples were dissolved in tetrahydrofuran and a corresponding amount of toluene was added.

TABLE 13

Example 5a. Number-average, weight-average and z-average molecular weight and polydispersity of adhesive compositions based on Cariflex TR 1107 (SIS three-block copolymer), which were heat-treated for a period between 120 and 360 minutes in the laboratory kneader. The adhesive composition was not stabilized with Irganox or argon

| sample taken | $M_n$ | $M_w$ | $M_z$ | $M_w/M_n$ |
|---|---|---|---|---|
| untreated | 159,048 | 197,247 | 239,912 | 1.240 |
| 120 minutes | 61,806 | 114,799 | 176,420 | 1.857 |
| 180 minutes | 46,679 | 84,497 | 133,398 | 1.810 |
| 240 minutes | 39,377 | 69,338 | 109,044 | 1.760 |
| 300 minutes | 32,701 | 56,307 | 88,183 | 1.721 |
| 360 minutes | 28,134 | 46,600 | 71,924 | 1.656 |

TABLE 14

Example 5b. Number-average, weight-average and z-average molecular weight and polydispersity of adhesive compositions based on Kraton GX 1657 (SEBS three-block copolymer), which were heat-treated for a period between 120 and 360 minutes in the laboratory kneader. The adhesive composition was not stabilized with Irganox or argon

| sample taken | $M_n$ | $M_w$ | $M_z$ | $M_w/M_n$ |
|---|---|---|---|---|
| untreated | 98,396 | 121,378 | 142,518 | 1.233 |
| 120 minutes | 93,791 | 117,405 | 144,724 | 1.251 |
| 180 minutes | 96,591 | 119,772 | 141,034 | 1.239 |
| 240 minutes | 97,425 | 121,307 | 142,906 | 1.245 |
| 300 minutes | 95,941 | 119,673 | 141,184 | 1.247 |
| 360 minutes | 94,705 | 118,409 | 139,956 | 1.250 |

TABLE 15

Example 6a. Number-average, weight-average and z-average molecular weight and polydispersity of adhesive compositions based on GX 1657, which were heat-treated for a period between 120 and 360 minutes in the laboratory kneader. The adhesive composition was stabilized with Irganox and argon

| sample taken | $M_n$ | $M_w$ | $M_z$ | $M_w/M_n$ |
|---|---|---|---|---|
| 120 minutes | 93,080 | 163,146 | 223,606 | 1.752 |
| 180 minutes | 91,739 | 162,362 | 223,376 | 1.769 |
| 240 minutes | 92,601 | 165,590 | 230,121 | 1.788 |
| 300 minutes | 90,402 | 161,962 | 227,359 | 1.791 |
| 360 minutes | 90,922 | 163,664 | 228,981 | 1.800 |

TABLE 16

Example 6b. Number-average, weight-average and z-average molecular weight and polydispersity of adhesive compositions based on GX 1657, which were heat-treated for a period between 120 and 360 minutes in the laboratory kneader. The adhesive composition was stabilized with Irganox and argon

| sample taken | $M_n$ | $M_w$ | $M_z$ | $M_w/M_n$ |
|---|---|---|---|---|
| 120 minutes | 93,952 | 116,246 | 136,825 | 1.237 |
| 180 minutes | 93,569 | 115,310 | 135,493 | 1.232 |
| 240 minutes | 94,924 | 116,940 | 137,383 | 1,231 |
| 300 minutes | 94,536 | 117,397 | 139,381 | 1.241 |
| 360 minutes | 93,866 | 116,185 | 137,083 | 1.237 |

Tables 13 and 14 show the changes of the molecular weight distribution with the corresponding parameters for Examples 5a and 5b. The unstabilized adhesive composition based on Cariflex TR 1107 suffers significant degradation of the polymer during heat treatment, which is characterized by a shift of the molecular weight distribution toward lower molecular weights. In the case of the unstabilized adhesive composition based on GX 1657, the change is considerably smaller. Comparing the stabilized Examples 6a and 6b (Tables 15 and 16) with one another, it is noted that, here, too, the adhesive composition based on GX 1657 undergoes considerably lesser changes. Surprisingly, the stabilized formulation, Example 6a, is also considerably more liable to polymer degradation, especially when one compares the molecular weight distributions of the untreated polymer.

Formulations based on polymers which contain a saturated middle block show higher stability during processing in the hot-melt method. The amount of necessary stabilizers can be greatly reduced in comparison to the comparison polymers with unsaturated middle block. Since stabilizers and their derivatives can also be regarded as potential skin irritants, the contact hot-melt adhesive composition according to the invention presents advantages in this regard.

EXAMPLE 7

Nicotine patch

Kraton G 1657 (SEBS three-block copolymer), 1039.5 g, and 16.5 g of Irganox 1010 are heated in a kneader to 170°

C. (duration approximately 45 minutes). Then 1419 g of Regalrez 1094 (aliphatic hydrocarbon resin) and 561 g of Abitol (hydroabietyl alcohol) are added in succession in portions and mixed until a homogeneous mixture is obtained (duration approximately 240 minutes). Then 299.5 g of nicotine are dissolved in the clear melt under an inert gas at 150° C. by dropwise addition (duration approximately 30 minutes). The obtained 150° C. nicotine-containing contact hot-melt adhesive composition is pressed continuously through a nozzle slit and is applied at a rate of 5 m/minute at a thickness of approximately 150 μm onto a cooled, silicone-coated polyester film (protective layer). A 15 μm thick polyester film (backing layer) is laminated onto the open contact adhesive surface under cooling.

Individual patches of 16 cm² in size are stamped from the obtained laminate.

Comparison Example 7'

Placebo patch

The preparation is done according to Example 5, but without the addition of nicotine.

Dynamic-mechanical analysis

Determination of the modulus of elasticity

The modulus of elasticity G' of the nicotine and placebo patches produced according to Example 7 and 7' was determined with the aid of the DMTA equipment, Model Eplexor (made by Gabo) as a function of temperature. The measurement was carried out in the shear mode on 14×14 mm samples consisting of the adhesive film and backing layer, according to DIN 53513 at a frequency of 10 Hz. The temperature range studied was between −50° and 80° C.; the temperature was increased starting from −50° C. in steps of 1° C. The corresponding shear modulus G' of the sample was determined after equalization of the temperature.

The modulus G' thus determined was uniformly 1.1 E5 Pa at 32° C., that is, in the skin temperature region, both for the patches that contained active ingredient and the one that did not. Accordingly, this important parameter for the evaluation of the adhesive properties of the patch was not changed in spite of relatively high (approximately 8%) nicotine content in the contact hot-melt adhesive.

Comparison Example 8

Nicotine patch

Preparation from solution

A nicotine-containing contact adhesive composition consisting of 170 g of nicotine 350 g of Cariflex TR 1107 (polystyrene-polyisoprene-polystyrene three-block copolymer)

350 g Hercurez C (aliphatic hydrocarbon resin)

280 g Abitol (hydroabietyl alcohol)

450 g Elcema P050 (cellulose for binding the nicotine)

1.050 g of special benzine 80–110 as solvent is applied onto a silicon-coated, approximately 100 μm thick protective film, so that after the removal of the solvent a contact adhesive layer of approximately 77.75 g/m² results. Two of these adhesive layers are laminated onto one another with simultaneous replacement of one of the protective layers by a 20 μm thick polyester film, so that a nicotine patch with an adhesive film of approximately 155.5 g/m² is obtained.

Individual patches of a size of 16 cm² are stamped from the obtained laminate.

Active ingredient release

The measurement of the release of nicotine from Example 7 and Comparison Example 8 is carried out according to the USP XXII Paddle-Over-Disk method in water at 32° C. The amounts of nicotine released per 16 cm² after 1, 2 and 3 hours are determined by liquid chromatography. The results of the investigation are shown in Table 17. As the measured values show, the liberation of the easily volatile nicotine from the reservoir according to the invention is retarded significantly more strongly than in the Comparison Example.

TABLE 17

| | Release of nicotine | | |
|---|---|---|---|
| | mean liberation in mg/16 cm² after | | |
| test preparation | 1 h | 2 h | 3 h |
| Example 7 (n = 3) | 3.4 | 4.8 | 5.8 |
| Comparison Example 8 (n = 6) | 9.2 | 12.7 | 15.8 |

We claim:

1. An active ingredient patch for the controlled release of active ingredients to the skin, said patch having no water-swellable polymers added thereto, and consisting of a backing layer; a water-insoluble adhesive film bonded to the backing layer and consisting of an active-ingredient-containing contact hot-melt adhesive; and a removable layer covering the adhesive film, wherein the film of active-ingredient-containing contact hot-melt adhesive is a chemically saturated three-block copolymer of polystyrene-block-copoly(ethylene-butylene)-block-polystyrene, in a concentration of 10 to 80 weight %, and an active ingredient which is low-melting or volatile and is liquid at the processing temperature of the contact hot-melt adhesive, at a concentration of 2.5 to 25 weight %.

2. The active ingredient patch according to claim 1, wherein the three-block copolymer is present in a concentration of 20 to 40 weight %.

3. The active ingredient patch according to claim 1, wherein styrene content of the three-block copolymer is 10 to 50 weight %.

4. The active ingredient patch according to claim 1, wherein styrene content of the three-block copolymer is 10 to 30 weight %.

5. The active ingredient patch according to claim 1, wherein nicotine is the active ingredient.

6. The active ingredient patch according to claim 1, wherein a β-receptor blocker is the active ingredient.

7. A method for the preparation of an active ingredient patch according to claim 1, wherein the contact hot-melt adhesive is mixed under heating to 100° to 200° C. in an inert gas atmosphere until a homogeneous melt is obtained, then the active ingredient is dissolved in the contact hot-melt adhesive under an inert gas at a processing temperature of 100° to 200° C., to form a homogeneous mixture and the homogeneous mixture is applied onto the covering layer, which is impermeable to the active ingredient.

8. A method for the preparation of an active ingredient patch according to claim 1, wherein the contact hot-melt adhesive is mixed, before addition of the active ingredient, by heating to 110° to 170° C. in an inert gas atmosphere until a homogeneous melt is obtained, then the active ingredient is dissolved in the contact hot-melt adhesive under an inert gas at a processing temperature of 110° to 130° C. to provide a homogeneous active-ingredient-containing contact hot-melt adhesive composition.

9. A method for the preparation of an active ingredient patch according to claim 8, wherein the homogeneous active-ingredient-containing contact hot-melt adhesive composition is applied onto the removable layer by extrusion, casting, roll application, blade application, spraying or by a pressure process, and is covered with the backing layer.

10. A method for the preparation of an active ingredient patch according to claim 8, wherein the homogeneous active-ingredient-containing contact hot-melt adhesive composition is applied onto the backing layer by extrusion, casting, roll application, blade application, spraying or a pressure method, and is covered with the removable layer.

11. A method for the preparation of an active ingredient patch according to claim 1, wherein division of the active ingredient patch is done by cutting or format stamping.

12. An active ingredient patch for the controlled release of active ingredients to the skin, said patch having no water-swellable polymers added thereto, and consisting of a backing layer; a water-insoluble adhesive film bonded to the backing layer and consisting of an active-ingredient-containing contact hot-melt adhesive; and a removable layer covering the adhesive film, wherein the active-ingredient-containing contact hot-melt adhesive is 10 to 80 weight % chemically saturated three-block copolymer of polystyrene-block-copoly-(ethylene-butylene)-block-polystyrene, 20 to 90 weight % tackifiers, 0 to 1 weight % antiaging agent, and 2.5 to 25 weight % of an active ingredient which is low-melting or volatile and is liquid at the processing temperature of the contact hot-melt adhesive.

13. The active ingredient patch according to claim 12, wherein the contact hot-melt adhesive contains 40 to 70 weight % tackifier.

14. The active ingredient patch according to claim 12, wherein the contact hot-melt adhesive contains aliphatic or aromatic hydrocarbon resins as the tackifier, said tackifier being compatible with the end blocks or the middle block of the three-block polymer.

15. The active ingredient patch according to claim 12, wherein the contact hot-melt adhesive contains hydroabietyl alcohol as the tackifier.

16. The active ingredient patch according to claim 13, wherein the contact hot-melt adhesive contains 0.1 to 1 weight % antiaging agent.

* * * * *

UNITED STATES PATENT AND TRADEMARK OFFICE
CERTIFICATE OF CORRECTION

PATENT NO.    : 5,527,536
DATED         : June 18, 1996
INVENTOR(S)   : Hans P. Merkle et al.

It is certified that error appears in the above-identified patent and that said Letters Patent is hereby corrected as shown below:

Column 6, last line in Table 1, "1f (1f)" should be --1f (1f')--.

Column 10, line 12,"i Hz" should be --1 Hz--.

Column 12, line 26, "Regalfez" should be --Regalrez--.

Signed and Sealed this

Tenth Day of September, 1996

Attest:

BRUCE LEHMAN

*Attesting Officer*                *Commissioner of Patents and Trademarks*